United States Patent
Thomas

(10) Patent No.: US 10,369,228 B2
(45) Date of Patent: Aug. 6, 2019

(54) METHOD AND COMPOSITION FOR ALLEVIATING OR PREVENTING ISCHEMIC TISSUE DAMAGE

(71) Applicant: Jeffrey E. Thomas, Hillsborough, CA (US)

(72) Inventor: Jeffrey E. Thomas, Hillsborough, CA (US)

(*) Notice: Subject to any disclaimer, the term of this patent is extended or adjusted under 35 U.S.C. 154(b) by 0 days.

(21) Appl. No.: 14/811,024

(22) Filed: Jul. 28, 2015

(65) Prior Publication Data

US 2015/0335758 A1    Nov. 26, 2015

Related U.S. Application Data

(63) Continuation of application No. 12/412,011, filed on Mar. 26, 2009, now abandoned.

(51) Int. Cl.
| | | |
|---|---|---|
| *A61K 47/46* | (2006.01) | |
| *A61K 31/198* | (2006.01) | |
| *A61K 31/21* | (2006.01) | |
| *A61K 33/26* | (2006.01) | |
| *A61K 47/26* | (2006.01) | |
| *A61K 9/00* | (2006.01) | |

(52) U.S. Cl.
CPC ............ *A61K 47/46* (2013.01); *A61K 9/0019* (2013.01); *A61K 9/0085* (2013.01); *A61K 31/198* (2013.01); *A61K 31/21* (2013.01); *A61K 33/26* (2013.01); *A61K 47/26* (2013.01)

(58) Field of Classification Search
None
See application file for complete search history.

(56) References Cited

U.S. PATENT DOCUMENTS

| | | |
|---|---|---|
| 3,557,787 A | 1/1971 | Cohen |
| 3,570,486 A | 3/1971 | Engelsher et al. |
| 3,678,931 A | 7/1972 | Cohen |
| 3,680,558 A | 8/1972 | Kapelowitz |
| 3,682,174 A | 8/1972 | Cohen |
| 3,749,084 A | 7/1973 | Cucchiara |
| 4,171,698 A | 10/1979 | Genese |
| 4,861,335 A | 8/1989 | Reynolds |
| 5,385,940 A | 1/1995 | Moskowitz |
| 5,429,603 A | 7/1995 | Morris |
| 5,496,284 A | 3/1996 | Waldenburg |
| 5,792,103 A | 8/1998 | Schwartz et al. |
| 5,820,583 A | 10/1998 | Demopulos et al. |
| 6,086,866 A | 7/2000 | Kouri |
| 6,358,536 B1 | 3/2002 | Thomas |
| 6,796,966 B2 | 9/2004 | Thomas |
| 2003/0026849 A1 | 2/2003 | Thomas |
| 2003/0199086 A1 | 10/2003 | Wieloch et al. |
| 2003/0219494 A1 | 11/2003 | Smith et al. |

FOREIGN PATENT DOCUMENTS

WO    90/00390    1/1990

OTHER PUBLICATIONS

Kloss, T., et al., "Delayed Respiratory Arrest Following Spinal Anesthesia," Abstract, Reg Anaesth., Jul. 7, 1984, 1 pg.
Niwa, et al., "Blockade of Nitric Oxide Synthesis in Rats Strongly Attenuates the CBF Response to Extracellular Acidosis," Journal of Cerebral Blood Flow and Metabolism, vol. 13, 1993, pp. 535-539.
Wang, et al., "Society of Neurosurgical Anesthesia and Critical Care," Journal of Neurosurgical Anesthesiology, Nov. 4, 1996, p. 323.
Lui, et al., "Reports of Investigation-Densities of Cerebrospinal Fluid and Spinal Anaesthetic Solutions in Surgical Patients at Body Temperature," Canadian Journal of Anaesthesia (1998), vol. 45, No. 4, pp. 297-303.
Dijkema, L.M., et al., "Case Report-Total Spinal Anaesthesia," Update in Anaesthesia, Issue 14 (2002) Article 14, pp. 1-3.
Thomas, Jeffrey E., et al., "Safety of Intraventricular Sodium Nitroprusside and Thiosulfate for the Treatment of Cerebral Vasospasm in the Intensive Care Unit Setting," Journal of the American Heart Association, vol. 33(2), Feb. 1, 2002, pp. 486-492.
Xu, et al., "Influence of the Glia Limitans on Pial Arteriolar Relaxation in the Rat," American Journal of Physiology-Heart and Circulatory Physiology, vol. 287:H331-H339, Feb. 12, 2004, 10 pgs.
Munis, James R., et al., "Delayed Emergence from Anesthesia Associated with Absent Brainstem Reflexes Following Suboccipital Craniotomy," Neurocritical Care Humana Press Inc., vol. 5 (2006), pp. 206-209.
Newman, B., et al., "Complete Spinal Block Following Spinal Anaesthesia," Anaesthesia Tutorial of the Week 180, May 24, 2010, pp. 1-4.
E. Levin, et al., "Density of Normal Human Cerebrospinal Fluid and Tetracaine," PubMed, U.S. National Library of Medicine, Anesth Analg. Nov. 1981; 60(11):814-7; 2 pages.
G.A. McLeod, "Density of Spinal Anaesthetic Solutions of Bupivacaine, Levobupivacaine, and Ropivacaine With and Without Dextrose," BJA: British Journal of Anaesthesia, vol. 92, Issue 4, Apr. 1, 2004, 101 pages.

*Primary Examiner* — Hasan S Ahmed
*Assistant Examiner* — Frank Choi
(74) *Attorney, Agent, or Firm* — Benesch, Friedlander, Coplan & Aronoff LLP

(57) ABSTRACT

A method for increasing collateral circulation includes providing a pharmaceutically acceptable synthetic cerebrospinal fluid that has a density different than that of the patient's naturally-occurring cerebrospinal fluid. The synthetic cerebrospinal fluid includes a vasodilator. The method further includes administering the synthetic cerebrospinal fluid to an intrathecal space of a patient through a lumbar access point to reach the intrathecal space of a patient.

11 Claims, 2 Drawing Sheets

METHOD AND COMPOSITION FOR ALLEVIATING OR PREVENTING ISCHEMIC TISSUE DAMAGE

RELATED APPLICATION DATA

This application is a continuation of pending U.S. application Ser. No. 12/412,011 filed Mar. 26, 2009.

BACKGROUND OF THE INVENTION

This application relates in general to compositions and methods for alleviating or preventing ischemic tissue damage.

Ischemia is a restriction in blood supply, generally due to factors in the blood vessels, with resultant damage or dysfunction of tissue. Ischemia in brain tissue may be caused by stroke or head injury. Collateral circulation is a process in which compensatory circulation is carried out when small (normally closed) vessels open and connect two larger vessels or different parts of the same artery after an obstruction of the principal vessel supplying the blood flow has occurred. The collateral vessels then serve as alternate routes of blood supply. All people have collateral vessels, at least in microscopic form, but these vessels are normally closed. They can, however, grow and enlarge in some people with coronary heart disease or other blood vessel disease, such as in the case of stroke. Although all patients have collateral vessels, the vessel do not necessarily open and varying numbers of the vessels may open.

When an artery in the brain is blocked due to stroke or transient ischemic attack (TIA), open collateral vessels can allow blood to bypass the blockage. This collateral circulation restores blood flow to the affected part of the brain. Because not all patients naturally develop collateral circulation, it is desirable to develop methods of treatment that will increase the likelihood that collateral circulation will occur.

DESCRIPTION OF THE DRAWINGS

The accompanying drawings, which are incorporated in and constitute a part of the specification, illustrate various example systems, methods, and so on, that illustrate various example embodiments of aspects of the invention. It will be appreciated that the illustrated element boundaries (e.g., boxes, groups of boxes, or other shapes) in the figures represent one example of the boundaries. One of ordinary skill in the art will appreciate that one element may be designed as multiple elements or that multiple elements may be designed as one element. An element shown as an internal component of another element may be implemented as an external component and vice versa. Furthermore, elements may not be drawn to scale.

DETAILED DESCRIPTION

Figure 1:
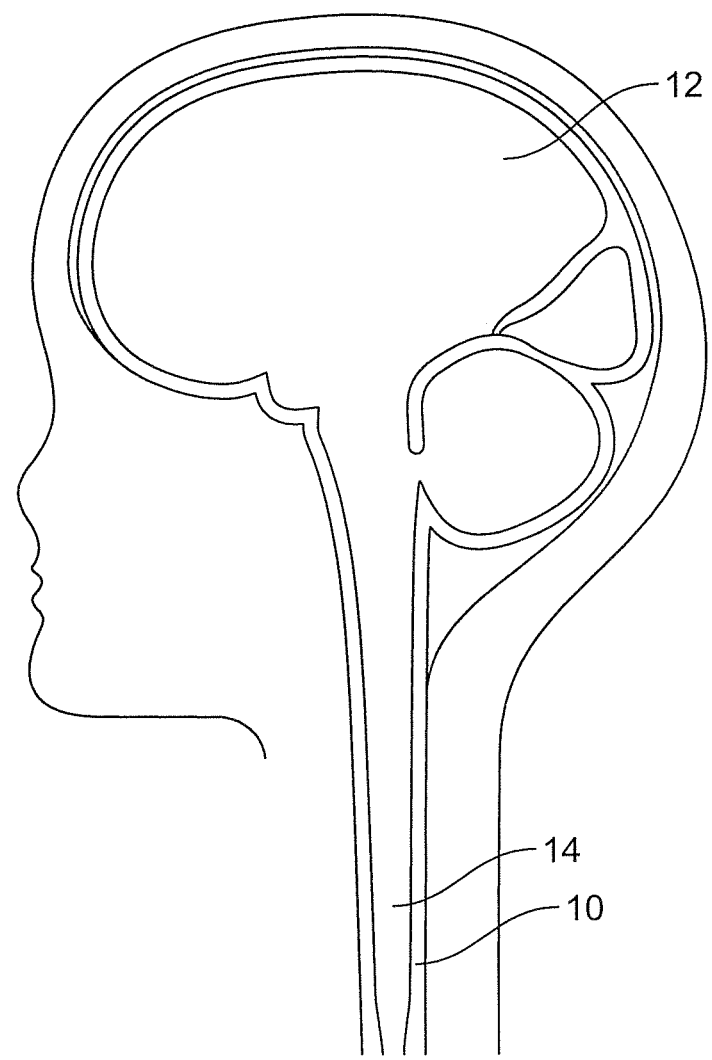
FIG. 1 is a cross sectional view of the central nervous system, head, and spine.

One embodiment of a composition for alleviating or preventing ischemic tissue damage includes a treatment solution comprising a hyperbaric cerebrospinal fluid and a vasodilator, specifically a NO donor compound. Naturally-occurring cerebrospinal fluid (CSF) is a clear liquid that occupies the subarachnoid space and the ventricular system around the inside of the brain and the intrathecal space around the spinal cord. CSF acts as a cushion or buffer for the cortex, providing a basic mechanical and immunological protection to the brain inside the skull. CSF also functions to bring nutrients to the brain and spinal cord. As shown in FIG. 1, CSF 10 may be an ideal carrier for neuroprotective agents and other such neurological treatments because, unlike blood, it directly contacts and circulates around the tissues of the brain 12, the spinal cord 14, and the blood vessels surrounding the brain. The treatment solution may comprise the patient's own CSF or it may be synthetic (sCSF).

The treatment solution generally contains a synthetic cerebrospinal fluid and a vasodilator. One example of a suitable vasodilator may be a nitric oxide (NO) donor compound. The NO donor compound can be any compound which, under physiological conditions in the tissue of the mammal to which the compound is to be administered, decomposes or otherwise reacts to generate NO. Physiological conditions in numerous mammalian tissues under a wide variety of circumstances are known, and the physiological conditions in previously non-characterized tissues or instances can be readily determined by the skilled artisan using well known techniques. Examples of NO donor compounds which are contemplated for use in the compositions, methods, apparatus, and kits of the invention include one or more of nitroglycerine, nitroprusside, a nitroprusside salt such as sodium nitroprusside, arginine, or another NO-generating compound, and mixtures thereof. Specifically, sodium nitroprusside is contemplated in one embodiment.

Compounds which are not known to be NO donor compounds at the time the present disclosure was prepared can nonetheless be used as soon as their NO-generating properties are known, since the precise chemical identity of the NO donor compound of the invention is not critical. Where more than one NO donor compound is administered to a subject, the multiple compounds can, for example, be administered either in admixture, separately but simultaneously, or sequentially. An NO donor compound can be modified so as to constitute a formulation comprising multiple molecules of nitric oxide per single molecule of the carrier compound, e.g. a branched molecule preparation. Surprisingly, the circulation in the collateral arteries is thought to be increased by adventitially administering a vasodilating compound to the subarachnoid space. In the central nervous system, the subarachnoid space is the compartment within the spinal column that contains the CSF.

The baricity of the treatment solution may also be altered, depending on the specific patient and area to be targeted by the cerebrospinal fluid composition. Posture (e.g. head-down position) of the patient and baricity of the solution is important during induction of cerebrospinal fluid with vasodilators to estimate the spread around the tissue of the brain and the blood vessels that surround it. The distribution of the solution may be estimated from the baricity of the solution. Baricity is the ratio of the density (mass/volume) of the sCSF solution to the density of the patient's natural cerebrospinal fluid. Thus, baricity influences the degree and rate of the spread of the sCSF because gravity causes hyperbaric solutions to flow downward in the naturally-occurring CSF, whereas hypobaric solutions tend to flow upward. In contrast, gravity has no effect on the distribution of isobaric solutions.

Generally, naturally-occurring CSF generally has a density of between 1.0063 to 1.0075 g/ml at 37° C. Generally, hyperbaricity is assumed if the density of a solution exceeds the density of the patient's CSF. A solution is hypobaric when the density is below the density of the patient's CSF. The density of naturally occurring CSF is generally unique to each patient. Thus, the baricity of the treatment solution may require adjustment to suit an individual patient's CSF density. In order to adjust the baricity of the treatment solution, different amounts of one or more density altering agents may be added to the treatment solution solution. One example of a suitable density altering agent is dextrose. For example, it is contemplated that 1 liter of the solution would contain about 5 to about 10% dextrose by volume (g/dL) to create a hyperbaric solution. Generally, a solution of at least 7.5% dextrose will be hyperbaric with respect to CSF. Any other suitable, metabolizable, density altering agent may be used.

Figure 2:
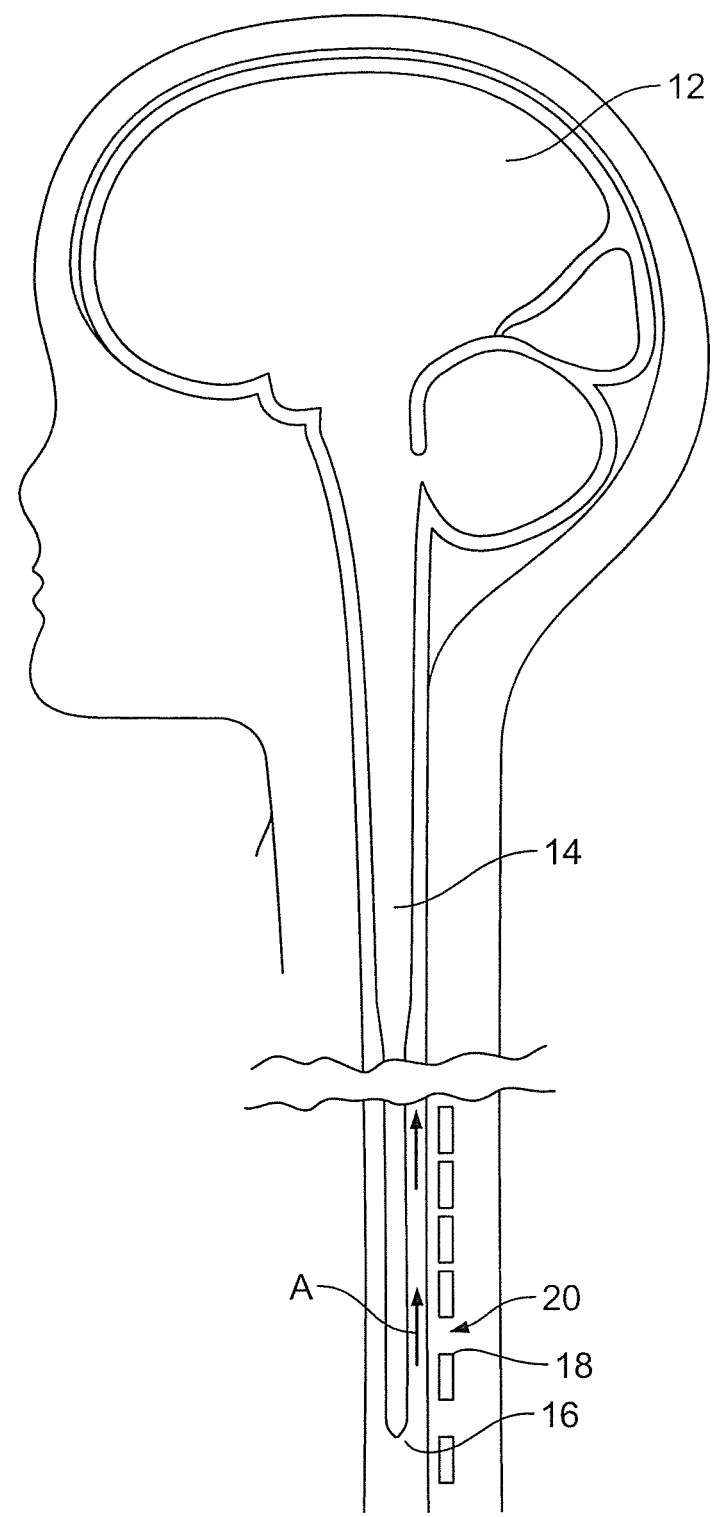
FIG. 2 is a schematic representation of a lumbar administration route.

Also contemplated is a method of increasing collateral circulation in a patient by providing a pharmaceutically acceptable synthetic cerebrospinal fluid which is hyperbaric or hypobaric with respect to naturally-occurring cerebrospinal fluid. The synthetic cerebrospinal fluid further includes a vasodilator. As shown in FIG. 2, the fluid can be administered to an intrathecal space 16 of a patient through a lumbar access point 20 between the vertebrae 18. The fluid can then travel throughout the central nervous system such as by the route indicated by arrow A and circulates around the spinal cord 14 and brain tissue 12. Access to the intrathecal space is often attempted below the L1 lumbar vertebrae level to minimize the risk of direct damage to the spinal cord by the needle. The speed and range of distribution of the sCSF solution after administration depends, to an extent, on the patient's position. For instance, a hyperbaric solution is denser than naturally occurring CSF and will tend to flow downward in accord with gravity. Conversely, a hypobaric solution will tend to flow upward against gravity. Adjusting a patient's position after injection of a hyperbaric solution may encourage or limit spread. If a broader or faster distribution of the treatment solution is required, the patient can be placed in a head-down position if using a hyperbaric solution. It should be recognized that the treatment solution may be administered to a brain or spinal tissue using any known method of accessing the CSF of a patient including, but not limited to lumbar access to the subarachnoid space, ventriculostomy, or by needle access to the cisterna magna.

The treatment solution may have a number of additional benefits such as having antiplatelet activity and countering microvascular sludging. The treatment solution may also include a neuroprotectant, such as spin trap agents, free radical scavengers, or anti-inflammatory agents. The treatment solution may also be altered to have an acidic pH.

The following two patients were treated using lumbar intrathecal administration of a site-specific pharmaceutical containing a vasodilator and sodium thiosulfate to the patient's own cerebrospinal fluid. Sodium nitroprusside was used as the vasodilator. The results of the patients' treatment with the sodium nitroprusside/sodium thiosulfate pharmaceutical composition provide the basis for the prophetic example utilizing the instant treatment solution and its method of use.

Patient A presented with aneurysmal subarachnoid hemorrhage. She was treated by endovascular microcoil embolization of her ruptured cerebral aneurysm. During the procedure an abrupt blood pressure elevation was noted that occurred simultaneously with loss of cortical evoked potentials that were being monitored during the case. Immediate angiographic injection demonstrated no cerebral blood flow above the skull base, and shift of injected contrast into the external carotid circulation. The diagnosis of rerupture of the aneurysm was made. Measures were immediately taken to complete the microcoil embolization procedure, which was rapidly accomplished (1-2 minutes). Microcatheter was withdrawn and attention was directed to ventriculostomy insertion. Intracranial pressure was high and immediately restored to normal range by rapid drainage of cerebrospinal fluid. This was followed in several (3-5) minutes by return of intraoperative neurophysiologic monitoring potentials.

The patient was recovering in the intensive care unit and began several days later to exhibit cerebral vasoconstriction (vasospasm), measured by transcranial Doppler examination. She was nevertheless awake, alert and extubated. She was able to give informed consent for the intrathecal treatment, which was administered by a ventriculostomy catheter.

The patient received injections every six hours of the pharmaceutical compound including sodium nitroprusside and sodium thiosulfate into their own cerebrospinal fluid. Mean transcranial doppler (TCD) velocities, used to indicate the presence of vascular narrowing, moved downward after the injections, and were maintained low as follows in Table 1.

The transcranial Doppler provides a number of ways to measure the flow patterns of cerebral arteries. The main parameters are mean flow velocity ($FV_m$), peak systolic flow velocity ($FV_s$), and end diastolic flow velocity ($FV_d$). These velocities tend to decrease as age increases. These values can be used to calculate the pulsatility index ($PI=(FV_s-FV_d)/FV_m$) and the resistance index ($RI=(FV_s-FV_d)/FV_s$) of the vessel. Evidence indicates that the PI has a strong correlation with the intracranial pressure and it is thought to be an indicator of resistance in the distal vasculature. The RI provides the technician with another way of measuring downstream vascular resistance. Both of these indices tend to increase as age increases. The Lindegaard index is a ratio that helps normalize the flow velocities between patients. In mild SAH-induced vasospasm, there is concern that mild elevations of blood flow velocities may not be secondary to the local vasospasm, but to an increase in systemic flow velocities. The Lindegaard index ($FV_{MCA}/FV_{ICA}$) is calculated by referencing the middle cerebral artery (MCA) FV with the FV of the extracranial, ipsilateral, internal carotid artery.

TABLE 1

| Date | High Mean MCA Left | Low Mean EX ICA Left | Lindegaard Index Ratio Left | High Mean MCA Right | Low Mean EX ICA Right | Lindegaard Index Ratio Right |
|---|---|---|---|---|---|---|
| Apr. 7, 2008 | 93 | 40 | 2.33 | 121 | 43 | 2.81 |
| Apr. 8, 2008 | 67 | 22 | 3.05 | 60 | 30 | 2.00 |
| Apr. 9, 2008 | 72 | 26 | 2.77 | 93 | 30 | 3.10 |
| Apr. 10, 2008 | 75 | 35 | 2.14 | 75 | 31 | 2.42 |

The patient reliably reported nausea after drug administration, which was treated prophylactically with ondansetron. Because of this symptom, drug administration was changed to a continuous infusion instead of periodic dosing. The patient's nausea was substantially improved following this intervention.

Following each injection, a decrease in TCD velocity was observed. The effect was not sustained, suggesting that the vasospasm was a chronic process amenable to interruption with the site-specific vasodilator. The overall effect was that the TCD velocities were restored to normal and maintained at these levels for the duration of the period of peak risk for delayed cerebral vasoconstriction (7 to 10 days following aneurysm rupture).

Patient B was admitted to hospital after sustaining rupture of a cerebral aneurysm. The aneurysm was treated by craniotomy and clip ligation. A lumbar drainage catheter was installed during operation, and remained in place in the intensive care unit. The patient's family gave informed consent for drug administration, which was performed through the lumbar drainage catheter.

Because the patient was considered at high risk for chronic delayed vasoconstriction, the medication was administered prophylactically. It was administered on a continuous basis through the lumbar intrathecal route. The patient did not manifest vasospasm. Following the end of the high-risk period for vasospasm (3-14 days following aneurysm rupture), the medication was discontinued without complication.

In both patient A and B, the effect of the pharmaceutical composition against cerebral vasoconstriction was observed. In Patient A, a manifest in the reversal of the established condition was observed and in Patient B, an apparent prevention of vasospasm was observed. The effect observed appears to be equally valid for the lumbar intrathecal route of administration as for the intraventricular route. The intraventricular route has been clinically validated in human studies (Thomas et al., 1999, 2001).

Prophetic Example

It is contemplated that use of the treatment solution described herein would have been useful in treating patients A and B. Specifically, patients A and B could have been treated using by administering a treatment solution including a pharmaceutically acceptable synthetic cerebrospinal fluid which is hyperbaric with respect to the patient's naturally-occurring cerebrospinal fluid and a vasodilator. The treatment solution would be administered to intrathecal space of a patient using a lumbar access point to access said intrathecal space.

The effectiveness of the above described pharmaceutical composition is wholly or substantially dependent upon its circulation in the cerebrospinal fluid. Through the medium of the cerebrospinal fluid, the medication is delivered to the adventitial side of a cerebral blood vessel, thereupon causing dilation of the blood vessel, and thereby increasing regional cerebral blood flow. Thus, the treatment solution, with properties of inhibition of platelet aggregation, inhibition of microvascular sludging, and dilation of muscularized cerebral blood vessels, is more advantageously delivered in a fluid medium characterized by increased density by comparison to native cerebrospinal fluid. This property of increased density, achievable by addition of a density altering agent, such as dextrose, allows the distribution of the treatment solution to be controlled by way of intrathecal lumbar administration. Thus, both brain and spinal cord afflictions may be treated.

One example of a suitable hyperbaric treatment solution may include 1 liter of solution containing 124.00 mmol/L of sodium chloride (NaCl), 3.30 mmol/L potassium chloride (KCl), 1.25 mmol/L potassium dihydrogen phosphate ($KH_2PO_4$), 2.40 mmol/L magnesium sulfate ($MgSO_4$), 2.00 mmol/L calcium chloride ($CaCl_2$), 25.70 mmol/L sodium bicarbonate ($NaHCO_3$), 10.00 mmol/L glucose, and 4.0 mg/mL sodium nitroprusside. It is contemplated that the amount of sodium nitroprusside could range from 0.25-25.0 mg/mL. The solution is then adjusted to contain from about 5% to about 8.25% dextrose (g/dL), creating a hyperbaric solution, based on the gender, age, and weight of the patient.

While example methods and compositions have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, devices, and so on, described herein. Additional advantages and modifications will readily appear to those skilled in the art. Therefore, the invention is not limited to the specific details, the representative apparatus, and illustrative examples shown and described. Thus, this application is intended to embrace alterations, modifications, and variations that fall within the scope of the appended claims. Furthermore, the preceding description is not meant to limit the scope of the invention. Rather the scope of the invention is to be determined by the appended claims and their equivalents.

I claim:

1. A method for increasing collateral circulation in a patient comprising:
   providing a pharmaceutically acceptable synthetic cerebrospinal fluid comprising a density-altering agent, wherein the synthetic cerebrospinal fluid has a density different from a density of naturally-occurring cerebrospinal fluid, and wherein the density-altering agent comprises about 5 to about 8.25 percent by volume of dextrose;
   mixing a vasodilator with the synthetic cerebrospinal fluid; placing the patient in a head-down position, wherein the vasodilator is selected from at least one member of the group consisting of nitroglycerine, nitroprusside, a nitroprusside salt, sodium nitroprusside, arginine, and mixtures thereof, and
   administering said synthetic cerebrospinal fluid to an intrathecal space of the patient using a lumbar access point to access said intrathecal space, wherein the density of the synthetic cerebrospinal fluid is sufficient to enable the spread of the synthetic cerebrospinal fluid throughout the brain of the patient.

2. A method for treating an individual suspected of having a cerebrovascular event comprising:
   providing a quantity of synthetic cerebrospinal fluid having a density different from the density of the individual's naturally-occurring cerebrospinal fluid, wherein the quantity of synthetic cerebrospinal fluid comprises a density-altering agent comprising about 5 to about 8.25 percent by volume of dextrose;
   mixing a vasodilator with the quantity of synthetic cerebrospinal fluid to form a synthetic cerebrospinal fluid vasodilator mixture, wherein vasodilator comprises nitroglycerine, nitroprusside, a nitroprusside salt, sodium nitroprusside, arginine, and mixtures thereof;
placing the individual in a Trendelenburg position; and
administering the synthetic cerebrospinal fluid vasodilator mixture to an intrathecal space of the individual.

3. The method of claim 2, wherein the density of the synthetic cerebrospinal fluid is greater than the density of the individual's naturally-occurring cerebrospinal fluid.

4. The method of claim 2, wherein the density of the synthetic cerebrospinal fluid is less than the density of the individual's naturally-occurring cerebrospinal fluid.

5. The method of claim 2, further comprising establishing a path for communication of the mixture to the individual's subarachnoid space.

6. A method for treating or inhibiting ischemic damage comprising:
   providing a pharmaceutically acceptable carrier fluid having a first density, said first density being different than a specific density of a patient's naturally-occurring cerebrospinal fluid, wherein the carrier fluid comprises a density-altering agent comprising about 5 to about 8.25 percent by volume of dextrose;
   mixing a vasodilator with the said carrier fluid, wherein the vasodilator is selected from at least one member of the group consisting of nitroglycerine, nitroprusside, a nitroprusside salt, sodium nitroprusside, arginine, and mixtures thereof; and
   administering said carrier fluid to an intrathecal space of a patient placed in a Trendelenburg position; wherein said first density of said carrier fluid facilitates transfusion of the vasodilator throughout the intrathecal space of the patient.

7. The method of claim 6, wherein the vasodilator is present in amounts from about 0.25 mg/ml to about 4 mg/ml.

8. The method of claim 6, wherein the carrier fluid has an acidic pH.

9. The method of claim 6, wherein the carrier fluid further comprises a neuroprotectant.

10. The method of claim 9, wherein the neuroprotectant comprises spin trap agents, free radical scavengers, or anti-inflammatory agents.

11. The method of claim 6, wherein the method further comprises administering the carrier fluid to the intrathecal space of the patient using a lumbar access point to reach the intrathecal space.

\* \* \* \* \*